United States Patent
Anvekar et al.

(10) Patent No.: US 12,016,830 B2
(45) Date of Patent: *Jun. 25, 2024

(54) PHARMACEUTICAL COMPOSITIONS COMPRISING ISOTRETINOIN AND PROCESSES FOR PREPARATION AND USES THEREOF

(71) Applicant: Acrotech Biopharma Inc., East Windsor, NJ (US)

(72) Inventors: Ashish Anvekar, East Windsor, NJ (US); Nagaprasad Vishnubhotla, Hyderabad (IN); Arun Jana, West Bengal (IN)

(73) Assignee: Acrotech Biopharma, LLC, East Windsor, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/214,770

(22) Filed: Jun. 27, 2023

(65) Prior Publication Data

US 2024/0000722 A1    Jan. 4, 2024

(30) Foreign Application Priority Data

Jul. 1, 2022    (IN) .............................. 202221038020

(51) Int. Cl.
*A61K 31/07* (2006.01)
*A61K 9/48* (2006.01)

(52) U.S. Cl.
CPC ............ *A61K 31/07* (2013.01); *A61K 9/4825* (2013.01); *A61K 9/4833* (2013.01); *A61K 9/4858* (2013.01); *A61K 9/4875* (2013.01)

(58) Field of Classification Search
CPC .... A61K 31/07; A61K 9/4825; A61K 9/4833; A61K 9/4858; A61K 9/4875
See application file for complete search history.

(56) References Cited

U.S. PATENT DOCUMENTS

| 4,322,438 A | 3/1982 | Peck |
| 7,435,427 B2 | 10/2008 | Vanderbist |

| 2003/0077297 A1* | 4/2003 | Chen | A61K 38/13 424/400 |
| 2006/0034786 A1* | 2/2006 | Michelet | A61K 8/49 424/59 |
| 2007/0014847 A1* | 1/2007 | Ahmed | A61K 9/4891 424/456 |
| 2017/0326091 A1 | 1/2017 | Kumar | |
| 2017/0326092 A1* | 11/2017 | Venkateshwaran | A61K 47/32 |

FOREIGN PATENT DOCUMENTS

| CN | 105535979 A | 5/2016 |
| EP | 3257499 A1 | 12/2017 |
| WO | 9210996 A1 | 9/1992 |
| WO | 0025772 | 5/2000 |
| WO | 2010134047 | 11/2010 |
| WO | 2015/181802 | 12/2015 |
| WO | 2016/016742 | 2/2016 |
| WO | 2016/051288 | 4/2016 |
| WO | 2016/189481 | 12/2016 |

OTHER PUBLICATIONS

ACCUTANE (isotretinoin) label (2002).
ASCORBICA (isotretinoin) label (2019).
Cyrulnik, A, et al. "High-Dose Isotretinoin (Accutane) Therapy: Positive Results in Nodulocystic Acne," Pharmacy and Therapeutics 36.5 (2011): 294.
Tan, Jerry, and Sanja Knezevic. "Improving bioavailability with a novel isotretinoin formulation (isotretinoin-Lidose)." Skin Therapy letter 18.6 (2013): 1-3.
Sindi, Am et al., "Lyophilized Composite Loaded with Meloxicam-Peppermint Oil Nanoemulsion for Periodontal Pain," Polymers 13 (2021): 2317.
Layton, A. "The use of isotretinoin in acne," Dermato-Endocrinology 1:3 (2009): 162-169.
International Search Report Issued Nov. 13, 2023 for PCT/US2023/069155.

* cited by examiner

*Primary Examiner* — Robert A Wax
*Assistant Examiner* — Quanglong N Truong
(74) *Attorney, Agent, or Firm* — Greenberg Traurig, LLP

(57) ABSTRACT

The present invention provides a high-dose oral pharmaceutical composition and high drug loading of isotretinoin with low fill-weight, and smaller size capsules, and methods of preparation and use thereof.

18 Claims, No Drawings

PHARMACEUTICAL COMPOSITIONS COMPRISING ISOTRETINOIN AND PROCESSES FOR PREPARATION AND USES THEREOF

CROSS REFERENCE TO RELATED APPLICATION

This application claims the benefit of, and priority to, Indian Provisional Patent Application Serial No. 202221038020, filed on Jul. 1, 2022, the entire disclosure of which is hereby incorporated by reference in its entirety.

FIELD

The present disclosure relates to pharmaceutical compositions comprising high dose and high drug loading of isotretinoin or pharmaceutically acceptable salts or esters thereof as an active agent, processes of preparation thereof, and methods of using the same.

BACKGROUND

Isotretinoin (13-cis retinoic acid or 13-cis vitamin A) is a retinoid and found in small quantities naturally in the body. Isotretinoin, its isomers and some of its analogs are widely known to have therapeutic activity in the treatment of severe skin disorders like acne (such as nodular or conglobate acne or acne at risk of permanent scarring), lupus erythematous and icthyosis [Peck G. L. & DiGiovanna (1994) Synthetic retinoids in dermatology. In: Sporn, M. B., Roberts, A. B. & Goodman, D. S., eds. The Retinoids: Biology, Chemistry, and Medicine. 2nd Ed. New York, Raven Press, pp. 631-658]. It is also reported to be used in neuroblastoma of children, cutaneous T-Cell Lymphomas, squamous cell skin cancers and also being investigated for treating various other cancers [Hong W. K. & TM L. M. (1994) Retinoids and human cancer. In: Sporn, M. B., Roberts, A. B. & Goodman, D. S., eds. The Retinoids: Biology, Chemistry, and Medicine. 2nd Ed. New York, Raven Press, pp. 597-630].

In 1982, FDA approved the use of isotretinoin for the treatment of nodular acne in the capsule dosage form "ACCUTANE ® " for 10 mg, 20 mg and 40 mg strengths. Each capsule of ACCUTANE® contains beeswax, butylated hydroxyanisole, edetate disodium, hydrogenated soybean oil flakes, hydrogenated vegetable oil, and soybean oil. Isotretinoin, is highly lipophilic with low oral bioavailability. Its absorption is enhanced when taken with high fat meal. Oral bioavailability which depends on food intake can be highly variable, which can result in making the toxicity and teratogenicity associated with the isotretinoin unpredictable [Jerry Tan & Sanja Knezevic; Improving bioavailability with a novel isotretinoin formulation (isotretinoin-Lidose); Skin Therapy Lett. 2013 Sep-Oct; 18(6):1-3]. ABSORICA®, approved by FDA in 2012, is a hard gelatin capsule formulation of isotretinoin and purportedly has reduced food effect. ABSORICA® is available in 10 mg, 20 mg, 25 mg, 30 mg, 35 mg and 40 mg strengths.

U.S. Pat. No. 4,322,438, assigned to Hoffman-La Roche, discloses a method of treating nodulocystic and conglobate acne in humans by oral administration of 13-cis- retinoic acid in amounts and for periods of time which afford an effectively complete remission from the condition even after administration of the compound ceases.

PCT Publication No. WO 00/25772, filed by Hoffman-La Roche, relates to soft gel capsules of isotretinoin having improved bioavailability. This application discloses that the currently marketed ACCUTANE® formulation of isotretinoin has a mean particle size of 100 µm and has a bioavailability of only about 20%. It also discloses a process of further reducing the particle size of isotretinoin to a range of about 5 µm to about 30 µm, thereby improving the bioavailability of isotretinoin.

U.S. Pat. No. 7,435,427 and its family members disclose Isotretinoin formulations relating to the marketed formulation of ABSORICA®. These patents disclose capsules comprising semi-solid suspension of isotretinoin containing at least two lipidic excipients, one having a Hydrophilic-lipophilic balance (HLB) value equal to or greater than 10 and the other being an oily vehicle. These patents disclose the use of "Lidose technology" to provide a formulation of isotretinoin with enhanced bioavailability by preparation of a hard gelatin capsule filled with liquid or semi-liquid lipidic contents comprising active substance mixed with the melted excipient. The mixture is then filled into hard gelatin capsules and then cooled under specific and constant conditions.

PCT publication WO2015/181802 discloses an oral pharmaceutical composition of isotretinoin dissolved or dispersed in a liquid vehicle selected from water, a water-miscible solvent, and/or mixtures thereof and a carrier substrate with enhanced bioavailability. This enhancement in bioavailability of isotretinoin by the present invention can be directly correlated to dose reduction of isotretinoin.

PCT publication WO2016/051288 discloses a low dose oral pharmaceutical composition of isotretinoin and a pharmaceutically acceptable excipient in the form of a dispersion which is further filled into capsules with an equivalent efficacy at a lower dose of isotretinoin in comparison to the marketed ABSORICA® capsules.

PCT publication WO2016/016742 discloses an oral pharmaceutical composition of isotretinoin with a reduced food effect. The disclosed composition comprises isotretinoin, one or more surfactants having HLB value of 10 or greater and one or more co-solvents wherein said composition is substantially free of oil PCT publication WO2016/189481 discloses a once daily oral pharmaceutical composition of isotretinoin for better patient compliance. The oral pharmaceutical composition of the present invention may be a modified-release composition, or an immediate-release composition, or a combination thereof.

PCT publication WO2010/134047 discloses a liquid dosage form of isotretinoin solubilized in a lipophilic carrier or a combination of lipophilic/hydrophilic carriers for better bioavailability without the use of an additional surfactant or emulsifier and substantially free of an alcoholic carrier & exhibits no bitter taste.

The standard dosage range for isotretinoin is 0.5 to 1 mg/kg/day given in two divided doses for 15 to 20 weeks (ABSORICA® Label). However, adult patients whose acne is very severe with scarring or is primarily manifested on the trunk may require dose adjustments up to 2 mg/kg/day, as tolerated. Therefore, based on body weight, the patient with higher body weight and a severe condition may require up to 200 mg of Isotretinoin in two divided doses.

The highest isotretinoin dose strength available to patients is 40 mg, which is typically provided in a large capsule of size 00 and difficult to swallow. Further, for many patients more than one capsule is required to adjust the dosage of 0.5 to 1 mg/kg/day. Thus, for patients who require higher doses such as up to 200 mg per day at least three capsules are needed. This higher "pill burden" can result in reduced patient compliance, leading to relapse of the condition within 2 years, necessitating repeated medical intervention

[Amanda Cyrulnik, Aron Gewirtzman, Kate Viola and Steven Cohen; High-Dose Isotretinoin (Accutane) Therapy: Positive Results in Nodulocystic Acne; American Academy of Dermatology; In: Peter Sonnenreich; P T. 2011 May; 36(5): 294-296].

Thus, there is a need for higher dose formulations and high drug loading formulations having lower fill-weight, with a smaller capsule size, with comparable and/or better bioavailability.

SUMMARY

Formulations of the present disclosure enable patients to take a fewer number of capsule(s) and take smaller size capsule(s) when they need higher doses. Thus, disclosed compositions and methods have the potential to achieve better patient adherence while providing dosing flexibility to prescribers including smaller capsule size, higher dose formulations and high drug loading formulations.

The present disclosure provides high dose oral pharmaceutical compositions and high drug loading of isotretinoin or pharmaceutically acceptable salts or esters thereof with low fill weight and smaller size capsules (such as size 1, size 2, or size 3 or less) with comparable and/or better bioavailability, reduced food effect, fewer number of capsules required, and lower toxicity.

Disclosed oral pharmaceutical compositions comprise isotretinoin or pharmaceutically acceptable salts or esters thereof and other pharmaceutically acceptable excipients or carriers.

The present disclosure further provides oral pharmaceutical compositions comprising isotretinoin or pharmaceutically acceptable salts or esters thereof in the form of liquid or semi-solid medicament filled in capsule and a process for preparing such composition.

The present disclosure further provides processes for preparing the disclosed oral pharmaceutical compositions.

The present disclosure further provides methods of treating conditions and disorders such as skin disorders including acne, for example by administering disclosed pharmaceutical compositions orally to a patient in need thereof.

The present disclosure further provides methods comprising the use of the said oral pharmaceutical compositions for the treatment of acne conditions such as severe recalcitrant nodular acne, for example in patients 12 years of age and older.

DETAILED DESCRIPTION

Definitions

The term "about," as used herein, generally refers to a range of values ±10% of a specified value. The term "about," also refers within the pharmaceutically acceptable limits found in the United States Pharmacopeia (USP-NF 21), 2003 Annual Edition, or available at www.usp.org, for amount of active pharmaceutical ingredients. With respect to blood levels, "about" means within FDA acceptable guidelines.

"Administration," or "to administer" means the step of giving (i.e. administering) a pharmaceutical composition or active ingredient to a subject. The pharmaceutical compositions disclosed herein can be administered via a number of appropriate routs, including oral and intramuscular or subcutaneous routes of administration, such as by injection, topically, or use of an implant.

The term "AUC" refers to the area under the time/plasma concentration curve after administration of the pharmaceutical composition. $AUC_{0-\infty}$ denotes the area under the plasma concentration versus time curve from time 0 to infinity; $AUC_{0-t}$ denotes the area under the plasma concentration versus time curve from time 0 to time t.

The term "$C_{max}$" refers to the maximum concentration of isotretinoin in the blood following administration of the pharmaceutical composition. The pharmacokinetic and pharmacodynamic parameters of the pharmaceutical composition of the present invention, when administered in healthy human subjects in fed as well as fasting conditions are reported as area under the curve (AUC), maximum concentration ($C_{max}$) and time at maximum concentration ($T_{max}$).

The term "D10" refers to the particle size of isotretinoin where 10% (w/v) of the particles have a size less than the defined D10 value; "D50" refers to the particle size of isotretinoin where 50% (w/v) of the particles have a size less than the defined D50 value; "D90" refers to the particle size of isotretinoin where 90% (w/v) of the particles have a size less than the defined D90 value.

The phrase "food effect" as used herein means food-drug interactions which either decrease or increase the extent of drug absorption. It refers to a relative difference in AUC, $C_{max}$, and/or of a drug, when said drug or a formulation thereof is administered orally to a human, concomitantly with food or in a fed state as compared to the same values when the same formulation is administered in a fasted state or without food.

The phrase "high dose," as used herein, refers to a dose of isotretinoin wherein said dose is at least 45 mg, which is at least 12.5% higher than 40 mg, the highest dose presently approved as ABSORICA® and ACCUTANE®.

The term "isotretinoin" refers to isotretinoin in its crystalline or amorphous form or a mixture thereof.

The phrase "high drug load," as used herein, refers to the mass ratio of drug/isotretinoin or a pharmaceutically acceptable salt or ester thereof to drug-loaded composition/isotretinoin or a pharmaceutically acceptable salt or ester thereof and pharmaceutical excipients filled into capsule. The high drug loaded capsule contains a high mass ratio of drug to drug-loaded composition filled into capsule which ultimately results in smaller size capsule to fill the composition. Disclosed pharmaceutical compositions provide a ratio of isotretinoin or a pharmaceutically acceptable salt or ester thereof to isotretinoin or a pharmaceutically acceptable salt or ester thereof and pharmaceutically acceptable excipients is 0.20:1 or more.

"Patient" means a human or non-human subject receiving medical or veterinary care.

The phrase "pharmaceutically acceptable carrier" is art-recognized, and includes, for example, pharmaceutically acceptable materials, compositions or vehicles, such as a liquid or solid filler, diluent, excipient, solvent, or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, sunflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

"Pharmaceutical composition" means a formulation with an active ingredient. The word "formulation" means that there is at least one additional ingredient (such as, for example and not limited to, an albumin [such as a human serum albumin (HSA) or a recombinant human albumin] and/or sodium chloride) in the pharmaceutical composition in addition to an active ingredient. A pharmaceutical composition is therefore a formulation which is suitable for diagnostic, therapeutic or cosmetic administration to a subject, such as a human patient. The pharmaceutical composition can be in a lyophilized or vacuum dried condition, a solution formed after reconstitution of the lyophilized or vacuum dried pharmaceutical composition with saline or water, for example, or as a solution that does not require reconstitution. As stated, a pharmaceutical composition can be liquid, semi-solid, or solid. A pharmaceutical composition can be animal-protein free.

The term "stable," as used herein, refers to chemical stability, wherein not more than 1.5% w/w of total related substances are formed on storage under conditions as per the ICH guidelines. The conditions include accelerated conditions (temperature of 40° C. at a relative humidity of 75%) and long term stability conditions (temperature of 25° C. at a relative humidity of 60%) for a period of at least three months.

The term "$T_{max}$" refers to the time in hours when $C_{max}$ is achieved following administration of the pharmaceutical composition.

"Therapeutically effective amount" means the level, amount or concentration of an active ingredient needed to treat a symptom, disease, disorder, or condition without causing significant negative or adverse side effects.

"Treat," "treating," or "treatment" means an alleviation or a reduction (which includes some reduction, a significant reduction, a near total reduction, and a total reduction), resolution or prevention (temporarily or permanently) of an symptom, disease, disorder or condition, so as to achieve a desired therapeutic or cosmetic result, such as by healing of injured or damaged tissue, or by altering, changing, enhancing, improving, ameliorating and/or beautifying an existing or perceived disease, disorder or condition.

Compositions

The present disclosure provides embodiments comprising high dose oral pharmaceutical compositions comprising isotretinoin or pharmaceutically acceptable salts or esters thereof. Disclosed compositions can further comprise at least one pharmaceutically acceptable excipient or carrier.

In embodiments, the present disclosure provides high drug loaded oral pharmaceutical compositions comprising isotretinoin or pharmaceutically acceptable salts or esters thereof. Disclosed compositions can further comprise at least one pharmaceutically acceptable excipient.

In embodiments, the present disclosure provides high dose oral pharmaceutical compositions comprising:

a. at least 45 mg of isotretinoin or a pharmaceutically acceptable salt or ester thereof, which is at least 12.5% higher than 40 mg, the highest dose presently-approved for ABSORICA® and ACCUTANE®; and b. at least one pharmaceutically acceptable excipient;

wherein said composition, when administered orally with higher dose and minimum number of capsules, results in comparable or better efficacy, comparable and lower adverse effect profile.

In further embodiments, the present disclosure provides high drug loaded oral pharmaceutical compositions comprising:

a. 30 mg or 40 mg or 50 mg or 60 mg or more of isotretinoin or a pharmaceutically acceptable salt or ester thereof; and b. at least one pharmaceutically acceptable excipient, which is filled in to lower size capsule compared to approved ABSORICA® and ACCUTANE®;

wherein said composition provides easy to swallow capsule composition for individual who require two or more number of capsules need to be administered orally for dose adjustments up to 2 mg/kg/day for the treatment of acne, thereby enabling better patient compliance.

In embodiments, the present disclosure provides high dose oral pharmaceutical compositions comprising:

a. isotretinoin or a pharmaceutically acceptable salt or ester thereof at a dose that is from 12.5% to about 50% higher with respect to the highest available dose of marketed ABSORICA® capsule i.e. 40 mg;

b. and a pharmaceutically acceptable excipient;

wherein said composition, when administered orally with higher dose and minimum number of capsules, results in comparable or better efficacy, comparable and lower adverse effect profile.

In embodiments, the present disclosure provides high dose oral pharmaceutical compositions comprising isotretinoin or a pharmaceutically acceptable salt or ester thereof and a pharmaceutically acceptable excipient, wherein said composition exhibits reduced food effect and thus provides patients greater flexibility.

In embodiments, the present disclosure provides high drug loaded oral pharmaceutical compositions comprising isotretinoin or a pharmaceutically acceptable salt or ester thereof and a pharmaceutically acceptable excipient, wherein said composition exhibits reduced food effect and thus provides patients greater flexibility.

In disclosed embodiments, the present invention provides high dose oral pharmaceutical composition comprising:

a. isotretinoin or a pharmaceutically acceptable salt or ester thereof;

b. an oily/lipid vehicle;

c. surfactant;

d. co-surfactant;

e. antioxidant(s); and/or f. co-solvent.

In disclosed embodiments, the present invention provides high drug loaded oral pharmaceutical compositions comprising:

a. isotretinoin or a pharmaceutically acceptable salt or ester thereof;

b. an oily/lipid vehicle;

c. surfactant;

d. co-surfactant;

e. antioxidant(s); and/or f. co-solvent.

In disclosed embodiments, the composition comprises isotretinoin or a pharmaceutically acceptable salt or ester thereof in an amount of, for example, about 20 mg to about 100 mg. For example, in embodiments, said composition comprises isotretinoin or a pharmaceutically acceptable salt or ester thereof in an amount of about, for example, 30 mg, 35 mg, 40 mg, 45 mg, 50 mg, 55 mg, 60 mg, 65 mg, 70 mg, 75 mg, 80 mg, 85 mg, 90 mg, 95 mg or 100 mg.

In further embodiments, said composition comprises isotretinoin or a pharmaceutically acceptable salt or ester thereof in an amount of about 30 mg. In another embodiment, said composition comprises isotretinoin or a pharmaceutically acceptable salt or ester thereof in an amount of about 40 mg. In another embodiment, said composition comprises isotretinoin or a pharmaceutically acceptable salt or ester thereof in an amount of about 60 mg.

In disclosed embodiments, the pharmaceutical composition comprises isotretinoin or a pharmaceutically acceptable salt or ester thereof and a pharmaceutically acceptable excipient wherein the ratio of isotretinoin or a pharmaceutically acceptable salt or ester thereof to isotretinoin or a pharmaceutically acceptable salt or ester thereof and pharmaceutically acceptable excipients is 0.20:1 or more; 0.40:1 or more; 0.60:1 or more: 0.80:1 or more: 1:1 or more, preferably 0.24:1 or more.

In disclosed embodiments, the composition comprises isotretinoin or a pharmaceutically acceptable salt or ester thereof in an amount of, for example, about 10% w/w to about 90% w/w of the total composition, or in an amount of about 10% w/w to about 50% w/w of the total composition, or in an amount of about 10% w/w to about 40% w/w of the total composition, preferably in an amount of about 20% w/w to about 30% w/w of the total composition.

The present disclosure provides high drug loading of isotretinoin or a pharmaceutically acceptable salt or ester thereof with low fill weight and thereby enabling to fill the composition of isotretinoin or a pharmaceutically acceptable salt or ester thereof into smaller size capsules, for example, of size 1, size 2, size 3, or less.

The present disclosure provides high drug loaded composition of isotretinoin or a pharmaceutically acceptable salt or ester thereof wherein the dose of isotretinoin is 30 mg to 100 mg and having low fill weight in smaller size capsules such as size 1, size 2, size 3, or less compared to presently approved ABSORICA® and ACCUTANE®.

In one embodiment, said composition is in the form of a liquid, semi-solid, solution, suspension, emulsion, microemulsion, dispersion, self-emulsifying drug delivery systems (SEDDS®) or self-emulsifying microemulsion drug delivery system (SMEDDS®). The said composition is filled into capsules in a total fill weight of about 100 mg to about 250 mg, about 100 mg to about 200 mg or about 100 mg to about 150 mg.

In other embodiments, the composition comprises isotretinoin in crystalline form or amorphous form or a mixture of crystalline and amorphous forms.

In another embodiment, the composition comprises isotretinoin or a pharmaceutically acceptable salt or ester thereof in milled or unmilled form, wherein the particle size distribution of isotretinoin or a pharmaceutically acceptable salt or ester thereof is such that the D10 is less than, for example, 400 µm, less than 300 µm, less than 200 µm, less than 100 µm, less than 50 µm, less than 40 µm, less than 35 µm, less than 30 µm, less than 25 µm, less than 20 µm, less than 15 µm, or less than 10 µm; preferably less than 70 µm, less than 60 µm, less than 50 µm, less than 40 µm, less than 35 µm, less than 30 µm, less than 25 µm, less than 20 µm, less than 15 µm, or less than 10 µm.

In further embodiments, disclosed compositions isotretinoin or a pharmaceutically acceptable salt or ester thereof in milled or unmilled form wherein the particle size distribution of isotretinoin or a pharmaceutically acceptable salt or ester thereof is such that the D50 is less than, for example, 400 µm, less than 300 µm, less than 200 µm, less than 100 µm, less than 50 µm, less than 40 µm, less than 35 µm, less than 30 µm, less than 25 µm, less than 20 µm, less than 15 µm, or less than 10 µm; preferably less than 150 µm, less than 50 µm, less than 40 µm, less than 35 µm, less than 30 µm, less than 25 µm, less than 20 µm, less than 15 µm, or less than 10 µm.

In further embodiments, disclosed compositions isotretinoin or a pharmaceutically acceptable salt or ester thereof in milled or unmilled form wherein the particle size distribution of isotretinoin or a pharmaceutically acceptable salt or ester thereof is such that the D90 is less than 400 µm, less than 300 µm, less than 200 µm, less than 100 µm, less than 50 µm, less than 40 µm, less than 35 µm, less than 30 µm, less than 25 µm, less than 20 µm, less than 15 µm, or less than 10 µm; preferably less than 300 µm, less than 100 µm, less than 50 µm, less than 40 µm, less than 35 µm, less than 30 µm, less than 25 µm, less than 20 µm, less than 15 µm, or less than 10 µm.

In further embodiments, the oral pharmaceutical composition comprises isotretinoin and a pharmaceutically acceptable excipient filled into capsules of size 1 or less, size 2 or less, size 3 or less, size 4 or less, or size 5 or less.

In further embodiments, the oral pharmaceutical composition comprises isotretinoin and a pharmaceutically acceptable excipient filled into capsules, wherein the volume filled into the said capsule is about 0.50 mL or less, about 0.37 mL or less, about 0.30 mL or less, about 0.21 mL or less, about 0.13 mL or less.

In further embodiments, the oral pharmaceutical composition comprises isotretinoin and a pharmaceutically acceptable excipient filled into capsules, wherein the concentration of isotretinoin in the said capsule is between about 200 mg/ml to about 300 mg/ml, preferably between about 220 mg/ml to about 280 mg/ml, preferably between about 230 mg/ml to about 270 mg/ml, preferably between about 240mg/ml to about 260 mg/ml, preferably about 245 mg/ml, preferably about 250 mg/mL, preferably about 255 mg/ml.

In further embodiments, the oral pharmaceutical composition comprises isotretinoin and a pharmaceutically acceptable excipient filled into capsules, wherein the concentration of isotretinoin in the said capsule is at least 25% w/w or more.

In further embodiments, the oral pharmaceutical composition comprises isotretinoin and a pharmaceutically acceptable excipient, wherein the said composition having isotretinoin concentration between about 200 mg/ml to about 300 mg/ml; preferably between about 220 mg/ml to about 280 mg/ml, preferably between about 230 mg/ml to about 270 mg/ml, preferably between about 240 mg/ml to about 260 mg/ml, preferably about 245 mg/ml, preferably about 250 mg/mL, preferably about 255 mg/ml comprising:
  a. isotretinoin or a pharmaceutically acceptable salt or ester thereof;
  b. an oily/lipid vehicle;
  c. surfactant;
  d. co-surfactant;
  e. antioxidant(s); and/or
  f. co-solvent.

In further embodiments, the oral pharmaceutical composition comprises isotretinoin and a pharmaceutically acceptable excipient, wherein the said composition has capsule fill volume about 0.5 mL or less, about 0.37 mL or less, about 0.30 mL or less, about 0.21 mL or less, about 0.13 mL or less, comprising:
  a. isotretinoin or a pharmaceutically acceptable salt or ester thereof;
  b. an oily/lipid vehicle;
  c. surfactant;
  d. co-surfactant;
  e. antioxidant(s); and/or
  f. co-solvent.

In further embodiments, the oral pharmaceutical composition comprises isotretinoin and a pharmaceutically acceptable excipient, wherein the said composition is in suspension dosage form, comprising:
  a. isotretinoin or a pharmaceutically acceptable salt or ester thereof;
  b. an oily/lipid vehicle;
  c. surfactant;
  d. co-surfactant;
  e. antioxidant(s); and/or
  f. co-solvent;
wherein the said suspension composition has capsule fill volume about 0.5 mL or less, about 0.37 mL or less, about 0.30 mL or less, about 0.21 mL or less, about 0.13 mL or less, and
wherein the concentration of isotretinoin in the capsule is between about 200 mg/ml to about 300 mg/ml, preferably between about 220 mg/ml to about 280 mg/ml, preferably between about 230 mg/ml to about 270 mg/ml, preferably between about 240 mg/ml to about 260 mg/ml, preferably about 245 mg/ml, preferably about 250 mg/mL, preferably about 255 mg/ml.

In another embodiment, the oral pharmaceutical composition comprises isotretinoin and a pharmaceutically acceptable excipient, wherein the said composition is in suspension dosage form, comprising:
  a. isotretinoin or a pharmaceutically acceptable salt or ester thereof;
  b. an oily/lipid vehicle;
  c. surfactant;
  d. co-surfactant;
  e. antioxidant(s); and/or
  f. co-solvent;
wherein the ratio of isotretinoin or a pharmaceutically acceptable salt or ester thereof to isotretinoin or a pharmaceutically acceptable salt or ester thereof and a pharmaceutically acceptable excipient is 0.20:1 or more; 0.40:1 or more; 0.60:1 or more: 0.80:1 or more: 1:1 or more, or the like.

In another embodiment of the present invention, the oral pharmaceutical composition comprises isotretinoin and a pharmaceutically acceptable excipient, wherein the said composition is in suspension dosage form, comprising:
  a. isotretinoin or a pharmaceutically acceptable salt or ester thereof;
  b. an oily/lipid vehicle;
  c. surfactant;
  d. co-surfactant;
  e. antioxidant(s); and/or
  f. co-solvent,
wherein the isotretinoin or a pharmaceutically acceptable salt or ester thereof is present in concentration of about 25% or more.

In further embodiments, the oral pharmaceutical composition comprises isotretinoin and a pharmaceutically acceptable excipient filled into capsules of size 1 or less, size 2 or less, size 3 or less, size 4 or less, or size 5 or less, wherein said capsule with the said pharmaceutical composition is easy to swallow as compared to currently available isotretinoin oral pharmaceutical compositions including ABSORICA® and/or ACCUTANE®.

In further embodiments, the oily/lipid vehicle includes, but is not limited to, vegetable oils, hydrogenated vegetable oils, essential oil, digestible or non-digestible oils, groundnut oil, olive oil, peppermint oil, soya bean oil, kernel oil, almond oil, safflower oil, sunflower oil, palm oil, sesame oil, canola oil, corn oil, castor oil, coconut oil, cotton seed oil, grape seed oil, animal fats, fatty acids, fatty acid ester, fats, waxes, sucrose esters, glyceryl monooleate, Polyglycerol-3-oleate, Glyceryl monolinoleate, Mono & diglycerides, Polyglycerol 10-oleate and mixtures thereof.

In another embodiment, the oily/lipid vehicle is present in an amount of about 1% w/w to about 90% w/w by the total weight of the composition; preferably in an amount of about 5% w/w to about 90% w/w by the total weight of the composition; more preferably in an amount of about 5% w/w to about 80% w/w by the total weight of the composition; most preferably in an amount of about 5% w/w to about 75% w/w by the total weight of the composition.

In additional embodiments, the ratio of isotretinoin or a pharmaceutically acceptable salt or ester thereof to the oily vehicle ranges from about 1:10 to about 13:1, preferably about 1:9 to about 9:1, more preferably about 1:4 to about 4:1, more preferably about 1:1.

In additional embodiments, the ratio of isotretinoin or a pharmaceutically acceptable salt or ester thereof to isotretinoin or a pharmaceutically acceptable salt or ester thereof and pharmaceutically acceptable excipients ranges from 0.20:1 or more; 0.40:1 or more; 0.60:1 or more: 0.80 or more: 1:1 or more, preferably 0.24:1 or more.

In additional embodiments, the surfactant includes, but is not limited to, anionic, cationic, or non-ionic surfactants; sorbitan fatty acid esters; polysorbates prepared from lauric, palmitic, stearic, and oleic acids; polyoxyethylene monoesters such as polyoxyethyl ethylene monostearate, polyoxyethylene monolaurate, and polyoxyethylene monooleate; glycerol monostearate; sorbitan esters; polysorbate 80; polyoxyethylene sorbitan monooleate; polyoxyl stearate macrogol ethers; polyoxyethylene; macrogolglycerol esters; caprylocaproyl macrogol-8 glycerides; PEG-8 caprylic/capric glycerides; macrogol glycerol hydroxystearate; polyoxyl 35 castor oil; macrogol glycerolhydroxystearate; polyoxyl 40 hydrogenated castor oil; macrogolglycerides such as caprylocaproyl polyoxylglycerides, lauroyl polyoxylglycerides such as hydrogenated coconut oil PEG 1500 esters, Gelucire 44/14; and stearoyl polyoxylglycerides; PEG-8 beeswax; polyethyleneglycol derivatives; polyoxyethylene castor oil derivatives; polyoxyethylene alkyl ethers; polyoxyethylene stearates; mixture of glycerol monostearate and PEG-75 stearate beeswax; glyceryl monostearate polyoxylethylene stearates and mixture thereof.

In other embodiments, the surfactant is present in an amount of about 0.01% w/w to about 90% w/w by the total weight of the composition; preferably in an amount of about 10% w/w to about 85% w/w by the total weight of the composition; more preferably in an amount of about 10% w/w to about 80% w/w by the total weight of the composition; most preferably in an amount of about 10% w/w to about 70% w/w by the total weight of the composition.

In further embodiments, the co-surfactant includes, but is not limited to, anionic, cationic, or non-ionic surfactants; hydrophilic or hydrophobic; water dispersible or water soluble surfactants; fatty acid ester derivatives; propylene glycol esters of caprylic acid, mainly composed of monoesters and diesters, propylene glycol monocaprylate; sorbitan fatty acid esters, sorbitan monoisostearate, sorbitan monolaurate, sorbitan monooleate, sorbitan monopalmitate, sorbitan monostearate, sorbitan sesquiisostearate, sorbitan sesquioleate, sorbitan trilaurate, sorbitan trioleate, sorbitan tristearate; oleoyl polyoxylglycerides such as apricot kernel oil PEG 300 esters; Labrafil M1944CS, Acconon® AKG-6; macrogolglyceridorum oleates; peglicol-5-oleate; glycerol monocaprylocaprate, glyceryl caprylate/caprate, mono-diglyceride of medium chain fatty acids, glyceryl esters derivatives; propylene glycol esters of caprylic and capric acids, propylene glycol dicaprylocaprate, propylene glycol dicaprolate/dicaprate; linoleoyl polyoxylglycerides such as macrogolglyceridorum linoleates, corn oil PEG 300 esters, Labrafil® M 2125; lauroyl polyoxylglycerides such as hydrogenated palm/palm kernel oil PEG 300 esters, Labrafil® M2130 CS and mixture thereof.

In further embodiments, the co-surfactant is present in an amount of about 0.01% w/w to about 90% w/w by the total weight of the composition; preferably in an amount of about 5% w/w to about 85% w/w by the total weight of the composition; more preferably in an amount of about 5% w/w to about 80% w/w by the total weight of the composition; most preferably in an amount of about 5% w/w to about 50% w/w by the total weight of the composition.

In further embodiments, the surfactant and co-surfactant is present in an amount of about 0.01% w/w to about 90% w/w by the total weight of the composition; preferably in an amount of about 5% w/w to about 85% w/w by the total weight of the composition; more preferably in an amount of about 5% w/w to about 80% w/w by the total weight of the composition; most preferably in an amount of about 5% w/w to about 50% w/w by the total weight of the composition.

In further embodiments, the co-solvent includes, but is not limited to, alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols such as tetrahydrofurfuryl alcohol PEG ether or methoxy PEG; amides, such as 2-pyrrolidone, 2-piperidone, β-caprolactam, N-alkylpyrrolidone, N-hydroxyalkylpyrrolidone, N-alkylpiperidone, N-alkylcaprolactam, dimethylacetamide, dimethylformamide and polyvinylpyrrolidone; esters, such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, F-caprolactone and isomers thereof, δ-valerolactone and isomers thereof, β-butyrolactone and isomers thereof; and other solubilizers such as dimethyl isosorbide, N-methyl pyrrolidones, monooctanoin, diethylene glycol monoethyl ether, dimethyl sulfoxide (DMSO), water and mixture thereof.

In another embodiment, the co-solvent is present in an amount of about 1% w/w to about 90% w/w by the total weight of the composition; preferably in an amount of about 10% w/w to about 90% w/w by the total weight of the composition; more preferably in an amount of about 10% w/w to about 80% w/w by the total weight of the composition; most preferably in an amount of about 10% w/w to about 40% w/w by the total weight of the composition.

In other embodiments, the composition comprises an antioxidant and include, but are not limited to butylated hydroxyl anisole, butylated hydroxyl toluene, tocopherol, ascorbyl palmitate, ascorbic acid, sodium ascorbate, sodium metabisulfite, sodium sulfite, sodium thiosulfate, propyl gallate, and mixtures thereof. The antioxidant is present in an amount of about 0.05% w/w to about 1.00% w/w of the total weight of the composition.

In further embodiments, the composition comprises a chelating agents and include, but are not limited to, EDTA, disodium EDTA, calcium disodium edetate, tartaric acid, malic acid and citric acid. The chelating agent is present in an amount of about 0.05% w/w to about 1.00% w/w of the total weight of the composition.

In further embodiments, the composition comprises a precipitation inhibitors agents and include, but are not limited to, hypromellose (HPMC), hypromellose acetate succinate, hypromellose phthalate, poloxamer and their derivatives, cyclodextrin and their derivatives, polyvinyl caprolactam-polyvinyl acetate-polyethylene glycol graft copolymer, vinylpyrrolidone-vinyl acetate copolymer and mixtures thereof. The precipitation inhibitors is present in an amount of about 0.05% w/w to about 60% w/w of the total weight of the composition.

In further embodiments, the composition comprises other excipients like permeability enhancers, pH modifier, and complexation agent. Examples of suitable permeability enhancer include, but are not limited to, phospholipid and their derivatives, phosphatidylcholine, lecithin and their derivatives and mixtures thereof. Examples of suitable pH modifier include, but are not limited to, megulamine and their derivatives, sodium hydroxide and their derivatives, sodium bicarbonate and their derivatives and mixtures thereof. Examples of suitable complexation agent include, but are not limited to, cyclodextrin and derivatives, phospholipids and derivatives and mixtures thereof. These excipients can be present in the invention from about 5% w/w to about 70% w/w of the total weight of the composition.

Methods of Preparation

In another aspect, there is provided a process for the preparation of a high dose oral pharmaceutical composition comprising isotretinoin or a pharmaceutically acceptable salt or ester thereof and at least one pharmaceutical excipient, wherein the process comprises the steps of:
a. heating a mixture of oil, surfactant and co-surfactant at 40° C.-45° C.;
b. dissolving antioxidants to the mixture of step (i) at 40° C.-45° C. and then cooling to room temperature;
c. dispersing isotretinoin to step (ii) under stirring;
d. optionally, the step (iii) is followed by addition of co-solvent
e. optionally, the step (iii) is followed by milling;
filling the medicament of step (iii) or step (iv) or step (v) in hard gelatin capsule;
g. preparing a gelatin banding solution by soaking gelatin in water for 6 hours at room temperature, followed by addition of polysorbate 80 at temperature of 60±10° C.; and
h. banding the filled capsule of step (vi) with banding solution of step (vii).

In yet another embodiment, said oral pharmaceutical composition is stable when stored at temperature of 40° C. and 75% relative humidity or at temperature of 30° C. and 65% relative humidity or at temperature of 25° C. and 60% relative humidity for a period of at least three months or more.

In yet another embodiment, said oral pharmaceutical composition is stable when stored at temperature of 40° C. and 75% relative humidity or at temperature of 30° C. and 65% relative humidity or at temperature of 25° C. and 60% relative humidity for a period of at least six months or more.

In yet another embodiment, said oral pharmaceutical composition is stable when stored at temperature of 40° C. and 75% relative humidity or at temperature of 30° C. and 65% relative humidity or at temperature of 25° C. and 60% relative humidity for a period of at least twelve months or more.

In yet another embodiment, said oral pharmaceutical composition has the drug content between about 102% w/w to about 110% w/w during the stability period.

In yet another embodiment, said oral pharmaceutical composition has impurities such as tretinoin, impurity G (5,6-epoxy-13-cis retinoic acid) and unknown impurities below 1.5.

Methods of Treatment

The present disclosure provides methods of treating diseases normally treatable using isotretinoin or pharmaceutically acceptable salts or esters thereof. For example, in disclosed embodiments, the therapeutically effective dose of isotretinoin can be 30 mg or more; 40 mg or more; 50 mg or more; 60 mg or more. Disclosed methods comprise treatment of, for example, cancers, skin disorders, and the like.

In embodiments, the present disclosure provides methods of treating acne by administering to the individual in need thereof, a high dose oral pharmaceutical composition comprising isotretinoin or a pharmaceutically acceptable salt or ester thereof and pharmaceutically acceptable excipients.

In embodiments, the present disclosure provides methods of treating acne by administering to the individual in need thereof, a high drug loaded oral pharmaceutical composition comprising isotretinoin or a pharmaceutically acceptable salt or ester thereof and pharmaceutically acceptable excipients.

In another embodiment, the composition exhibits a ln-transformed geometric least square mean $C_{max}$ of about 915.3556 ng/mL under fed condition and a ln-transformed geometric least square mean $C_{max}$ of about 302.8420 ng/mL under fasting condition.

In another embodiment, the composition exhibits a ln-transformed geometric least square mean $AUC_{0 \to t}$ of about 15924.4305 ng·h/mL and $AUC_{0 \to \infty}$ of about 16953.5405 ng·h/mL under fed condition and a ln-transformed geometric least square mean $AUC_{0 \to t}$ of about 4911.7465 ng·h/mL and $AUC_{0 \to \infty}$ of about 5335.7760 ng·h/mL under fasting condition.

In another embodiment, the composition, when administered orally, has a mean fed/fasted ratio of $AUC_{0 \to t}$ and $AUC_{0 \to \infty}$ of about 1.5 and a mean fed/fasted ratio of ln-transformed geometric least square $C_{max}$ of about 2.25.

The invention may be further illustrated by the following examples, which are for illustrative purposes only and should not be construed as limiting the scope of the invention in anyway. Modification in examples fall within the scope and spirit of appended claims, and which would be obvious to a person skilled in the art based upon the disclosure herein, are also considered to be within the scope of this invention.

EXAMPLES

Example 1

The weight (wt) of active ingredients and excipients is expressed in milligrams (mg) and % is expressed in terms of % w/w in the composition. The examples are non-limiting and will apply to the entire range of invention in terms of quantity.

Composition

| Sr. No. | Ingredients | % w/w range |
|---|---|---|
| 1 | Isotretinoin or a pharmaceutically acceptable salt or ester thereof | 10-90 |
| 2 | Oily or lipid vehicle | 1-90 |
| 3 | Surfactant | 0.01-90 |
| 4 | Co-surfactant | 0.01-90 |
| 5 | Antioxidant(s) | 0.05-1 |
| 6 | Co-solvent | 0.01-90 |
| | Total | 100 |
| | Hard Gelatin Capsule shell Size 1 or 2 or 3 or 4 or 5 | |

Procedure for the preparation of composition:
(i) heating a mixture of oil, surfactant and co-surfactant;
(ii) dissolving antioxidants to the mixture of step (i);
(iii) dispersing isotretinoin or a pharmaceutically acceptable salt or ester thereof to step (ii) under stirring;
(iv) optionally, the step (iii) is followed by addition of co-solvent
(v) optionally, the step (iii) is followed by milling;
(vi) filling the medicament of step (iii) or step (iv) or step (v) in capsule;
(vii) preparing a gelatin banding solution by soaking gelatine in water, followed by addition of polysorbate;
(vii) banding the filled capsule of step (vi) with banding solution of step (vii).

Compositions Prepared Without Co-Solvents

TABLE 1

| | | Soyabean oil based | | Peceol based | | Peppermint oil based | |
|---|---|---|---|---|---|---|---|
| # | Ingredients | Wt (in mg) | % w/w range | Wt (in mg) | % w/w range | Wt (in mg) | % w/w range |
| 1 | Isotretinoin | 60.00 | 13.36-25.02 | 60.00 | 13.36-25.02 | 50.00-60.00 | 14.32-25.02 |
| 2 | Glyceryl monooleate (Type 40) (Peceol ®) | — | — | 60.00 | 13.36-25.02 | — | — |

TABLE 1-continued

|   | | Soyabean oil based | | Peceol based | | Peppermint oil based | |
|---|---|---|---|---|---|---|---|
| # | Ingredients | Wt (in mg) | % w/w range | Wt (in mg) | % w/w range | Wt (in mg) | % w/w range |
| 3 | Peppermint Oil | — | — | — | — | 37.00-60.00 | 14.32-25.02 |
| 4 | Soyabean oil | 37-60.00 | 13.36-25.02 | — | — | — | — |
| 5 | Polysorbate 80 (Tween ®/Montanox 80 ®) | 65-160.00 | 28-45.88 | 110.00-160.00 | 35-47 | 0.00-69.00 | 0-28.5 |
| 6 | Polyoxyl 35 castor oil (Kolliphore EL ®) | — | — | — | — | 50.00-115.00 | 26.25-45.88 |
| 7 | Poloxamer | | | | | 0.00-110.25 | |
| 8 | Propylene glycol monocaprylate (Type II) (Capryol 90 ®) | 8.75-75.00 | 3.65-30.55 | 8.00-18.00 | 3.0-4.0 | 8.75-75.00 | 3.65-30.69 |
| 9 | Caprylcaproyl Polyoxyl-8 glycerides USNF (Labrasol ® ALF) | 0-150.00 | 0-33.4 | 0.00-150.00 | 0-33.4 | 140.00-170.00 | 0-40.57 |
| 10 | Butylated hydroxy Anisole (BHA) | 0.50-1.20 | 0.10-0.50 | 0.50 | 0.11-0.20 | 0.40-0.50 | 0.12-0.20 |
| 11 | Butylated Hydroxy Toluene (BHT) | 0.40-0.50 | 0.10-0.20 | 0.50 | 0.11-0.20 | 0.40-0.50 | 0.12-0.20 |
| | Total | 239.75-449.00 | | 239.75-449.00 | | 185.00-419.00 | |
| 12 | Hard Gelatin Capsule shell Capsule Banding | | | Size 1 OR 2 | | | |
| 13 | Gelatin USNF (Gelatin 200-220 Bloom) | 3.30-5 | — | 3.30-5 | | 3.30-5 | |
| 14 | Polysorbate 80 USNF | 0.05-1 | — | 0.05-1 | | 0.05-1 | |
| 15 | Purified water USP@ | q.s. | — | q.s. | | q.s. | |

Compositions prepared with co-solvents

TABLE 2

|   | | Soyabean oil based | | Peceol based | | Peppermint Oil based | | | |
|---|---|---|---|---|---|---|---|---|---|
| # | Ingredient | Wt (in mg) | % w/w | Wt (in mg) | % w/w | Wt (in mg) | % w/w | Wt (in mg) | % w/w |
| 1 | Isotretinoin | 60.00 | 20.06 | 60.00 | 20.40 | 60.00 | 25.00 | 60.00 | 25.00 |
| 2 | Glyceryl monooleate (Type 40) (Peceol) | — | — | 59.787 | 20.33 | — | — | — | — |
| 3 | Peppermint Oil | — | — | — | — | 40.00 | 16.66 | 60.00 | 25.00 |
| 4 | Soyabean oil | 37.07 | 12.39 | — | — | — | — | — | — |
| 5 | Polysorbate 80 (Tween/Montanox 80) | 68.27 | | 110.472 | 37.57 | — | — | — | — |
| 6 | Polyoxyl 35 castor oil (Kolliphore EL) | — | — | — | — | 80.00 | 33.33 | 110 | 45.83 |
| 7 | Propylene glycol monocaprylate (Type II) (Capryol 90) | 73.66 | 24.63 | 8.741 | 2.97 | — | | 8.75 | 3.65 |

TABLE 2-continued

| # | Ingredient | Soyabean oil based Wt (in mg) | Soyabean oil based % w/w | Peceol based Wt (in mg) | Peceol based % w/w | Peppermint Oil based Wt (in mg) | Peppermint Oil based % w/w | Wt (in mg) | % w/w |
|---|---|---|---|---|---|---|---|---|---|
| 8 | Butylated hydroxy Anisole (BHA) | 0.50 | 0.16 | 0.50 | 0.17 | 0.50 | 0.20 | 0.5 | 0.21 |
| 9 | Butylated Hydroxy Toluene (BHT) | 0.50 | 0.16 | 0.50 | 0.17 | 0.50 | 0.20 | 0.5 | 0.21 |
| 10 | Isopropyl alcohol USP | 59.00 | 19.73 | 36.00 | 12.24 | 59.00 | 24.58 | — | — |
| 11 | Purified Water USP | — | — | 18.00 | 6.12 | — | — | — | — |
| | Total | 299.00 | 100.00 | 294.00 | 100.00 | 240.00 | 100.00 | 240 | 100 |
| 12 | Hard Gelatin Capsule shell | Size 2 | | Size 2 | | Size 2 | | Size 2 | |
| | Capsule Banding | | | | | | | | |
| 13 | Gelatin USNF (Gelatin 200-220 Bloom) | 3.00 | — | 3.00 | — | 3.00 | — | 4.76 | — |
| 14 | Polysorbate 80 USNF | 0.050 | — | 0.050 | — | 0.050 | — | 0.12 | — |
| 15 | Purified water USP@ | q.s. | — | q.s. | — | q.s. | — | q.s | — |

TABLE 3

| # | Ingredient | Wt (in mg) | % w/w |
|---|---|---|---|
| 1 | Isotretinoin | 22.5-75 | 18.75-31.25% |
| 2 | Peppermint Oil | 22.5-75 | 18.75-31.25% |
| 3 | Polyoxyl 35 castor oil (Kolliphore EL) | 41.98-137.5 | 34.37-57.29% |
| 4 | Propylene glycol monocaprylate (Type II) (Capryol 90) | 3.28-10.93 | 1.52-4.54% |
| 5 | Butylated hydroxy Anisole (BHA) | 0.18-0.625 | 0.15-0.26% |
| 6 | Butylated Hydroxy Toluene (BHT) | 0.18-0.625 | 0.15-0.26% |
| | Total | 90-299.68 | 100 |
| 7 | Hard Gelatin Capsule shell Capsule Banding | Size 2 or Size 3 | |
| 8 | Gelatin USNF (Gelatin 200-220 Bloom) | 5.95-3.57 | — |
| 9 | Polysorbate 80 USNF | 0.15-0.09 | — |
| 10 | Purified water USP@ | q.s | — |

TABLE 4

| # | Ingredient | 30 mg | 40 mg | 50 mg | 60 mg |
|---|---|---|---|---|---|
| 1 | Isotretinoin | 30.00 | 40.00 | 50.00 | 60.00 |
| 2 | Peppermint oil | 30.00 | 40.00 | 50.00 | 60.00 |
| 3 | Polyoxyl castor oil (Kolliphore ® EL) | 55.13 | 73.50 | 91.87 | 110.25 |
| 4 | Propylene glycol monocaprylate (Capryol 90) | 4.38 | 5.84 | 7.31 | 8.75 |
| 5 | Butylated hydroxy Anisole (BHA) | 0.25 | 0.33 | 0.41 | 0.50 |
| 6 | Butylated Hydroxy Toluene (BHT) | 0.25 | 0.33 | 0.41 | 0.50 |
| 7 | Gelatin capsule shell | Size 3 | Size 3 | Size 2 | Size 2 |
| | TOTAL | 120.00 | 160.00 | 200.00 | 240.00 |
| | Gelatin banding | | | | |
| 8 | Gelatin 180 bloom | 4.76 | 4.76 | 4.76 | 4.76 |
| 9 | Polysorbate 80 | 0.12 | 0.12 | 0.12 | 0.12 |
| 10 | Purified water | 0.38 | 0.38 | 0.38 | 0.38 |
| | TOTAL | 125.26 | 165.26 | 205.26 | 245.26 |

Procedure for the Preparation of the Examples in Tables 1, 2, 3 and 4

1. Mix surfactant and co-surfactant and heat together at 40° C.-45° C. till clear solution is formed.
2. Dissolve BHA & BHT to above at 40° C.-45° C. and then cool to room temperature and add oil.
3. Disperse isotretinoin to step 2 under stirring at room temperature.
4. Optionally, the step (3) is followed by milling. Mill the drug dispersion of step 3 by using dyno mill at optimum processing conditions, until PSD (d (0.9)) of NMT 80 micron is achieved.
5. Optionally, the step (3) is followed by addition of co-solvent
6. Fill the medicament in hard gelatin capsules.
7. Prepare the gelatin banding solution by soaking gelatin in water for specified hours at room temperature, than heat the gelatin mass to 60±10° C. followed by addition of polysorbate 80 to it at 60±5° C.
8. Band the filled capsules of step 6 by using banding solution of step 7.

Example 2

Ratio optimization study: Compositions of table 3 were prepared using ratio of isotretinoin or a pharmaceutically acceptable salt or ester thereof to peppermint oil (oily vehicle) which is 1:10, 1:9, 1:4, 13:1, 9:1, 4:1 and 1:1. The composition having 1:1 isotretinoin or a pharmaceutically acceptable salt or ester thereof to peppermint oil (oily vehicle) remains stable for accelerated and long term stability conditions. Related substances, known impurities and unknown impurities were measured and reported to be within the ICH guideline limits.

Example 3

Dissolution studies: Dissolution studies of the pharmaceutical compositions of Examples A and B were studied in Modified USP & Discriminatory dissolution media using USP Type II Apparatus. The % drug release with respect to time was studied.

Example 4

Stability studies: The stability of the pharmaceutical compositions of examples A and B in PVC-Aclar blister packaging were studied as per ICH guidelines at accelerated and long term stability conditions. Related substances, known impurities and unknown impurities were measured and reported to be within the ICH guideline limits.

Example 5

Clinical studies: The pharmacokinetic and pharmacodynamic parameters in the human volunteers of the Isotretinoin Capsules USP 60 mg compositions-Treatment-1 (T1) and Treatment-2 (T2) were studied and compared with currently approved ABSORICA® (Isotretinoin) Capsules [One 40 mg Capsule and two 10 mg Capsules] mentioned as Treatment R in below table.

Statistics of Pharmacokinetic Parameters of Isotretinoin Capsules USP 60 mg FED BE Study

| Parameters | Geometric Least Square Means | | | Intra Subject CV (%) |
| --- | --- | --- | --- | --- |
| | Treatment R | Treatment-1 (T1) | Treatment-2 (T2) | |
| $C_{max}$ (ng/ml) | 823.6562 | 886.5567 | 915.3556 | 25.1 |
| $AUC_{0-t}$ (hr · ng/ml) | 14078.4287 | 14799.4163 | 15924.4305 | 12.0 |
| $AUC_{0-\infty}$ (hr · ng/ml) | 15041.4269 | 15829.1076 | 16953.5405 | 12.1 |

| | Lntransformed Data | | | | |
| --- | --- | --- | --- | --- | --- |
| Parameters | (T1/R) Ratio % | 90% Confidence Interval (T1/R) | (T2/R) Ratio % | 90% Confidence Interval (T2/R) | Power % |
| $C_{max}$ | 107.64 | 93.24-124.26 | 111.13 | 96.26-128.30 | 82 |
| $AUC_{0-t}$ | 105.12 | 98.04-112.72 | 113.11 | 105.49-121.28 | 100 |
| $AUC_{0-\infty}$ | 105.24 | 98.08-112.91 | 112.71 | 105.05-120.93 | 100 |

Statistics of Pharmacokinetic Parameters of Isotretinoin Capsules USP 60 mg FASTING BE Study

| Parameters | Geometric Least Square Means | | | Intra Subject CV (%) |
| --- | --- | --- | --- | --- |
| | Treatment R | Treatment-1 (T1) | Treatment-2 (T2) | |
| $C_{max}$ (ng/ml) | 334.9585 | 298.4936 | 302.8420 | 24.1 |
| $AUC_{0-t}$ (hr · ng/ml) | 5370.6699 | 4071.6994 | 4911.7465 | 24.7 |
| $AUC_{0-\infty}$ (hr · ng/mL) | 5903.7534 | 4442.6349 | 5335.7760 | 24.5 |

| | Lntransformed Data | | | | |
| --- | --- | --- | --- | --- | --- |
| Parameters | (T1/R) Ratio % | 90% Confidence Interval (T1/R) | (T2/R) Ratio % | 90% Confidence Interval (T2/R) | Power % |
| $C_{max}$ | 89.11 | 77.24-102.81 | 90.41 | 78.37-104.31 | 83 |
| $AUC_{0-t}$ | 75.81 | 65.50-87.75 | 91.46 | 79.01-105.86 | 81 |
| $AUC_{0-\infty}$ | 75.25 | 65.08-87.01 | 90.38 | 78.16-104.50 | 82 |

Related Substances or Impurity data of Isotretinoin Capsules USP 60 mg Compositions—Treatment-1 (T1) and Treatment-2 (T2) at Accelerated Conditions

| | Treatment-1 (T1) | | | | Treatment-2 (T2) | | | |
| --- | --- | --- | --- | --- | --- | --- | --- | --- |
| Batch No | Initial | 1.5 M | 3 M | 6 M | Initial | 1.5 M | 3 M | 4.5 M |
| Tretinoin (NMT 0.5%) | ND | 0.06 | ND | 0.08 | 0.05 | 0.09 | 0.08 | 0.08 |
| Impurity G (NMT 0.8%) | 0.1 | 0.1 | 0.11 | 0.11 | 0.03 | 0.20 | 0.17 | 0.21 |
| Highest Unknown (NMT 0.2%) | 0.06 | 0.05 | 0.06 | 0.05 | 0.02 | ND | 0.05 | 0.05 |
| Total Impurities (NMT 1.5%) | 0.16 | 0.15 | 0.31 | 0.29 | 0.10 | 0.29 | 0.36 | 0.39 |

In closing, it is to be understood that although aspects of the present specification are highlighted by referring to specific embodiments, one skilled in the art will readily appreciate that these disclosed embodiments are only illustrative of the principles of the subject matter disclosed herein. Therefore, it should be understood that the disclosed subject matter is in no way limited to a particular methodology, protocol, and/or reagent, etc., described herein. As such, various modifications or changes to or alternative configurations of the disclosed subject matter can be made in accordance with the teachings herein without departing from the spirit of the present specification. Lastly, the terminology used herein is for the purpose of describing particular embodiments only, and is not intended to limit the scope of the present invention, which is defined solely by the claims. Accordingly, the present invention is not limited to that precisely as shown and described.

Certain embodiments of the present invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the present invention to be practiced otherwise than specifically described herein. Accordingly, this invention includes all modifications and equivalents of the subject matter recited in the claims appended hereto as permitted by applicable law. Moreover, any combination of the above-described embodiments in all possible variations thereof is encompassed by the invention unless otherwise indicated herein or otherwise clearly contradicted by context.

Groupings of alternative embodiments, elements, or steps of the present invention are not to be construed as limitations. Each group member may be referred to and claimed individually or in any combination with other group members disclosed herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Unless otherwise indicated, all numbers expressing a characteristic, item, quantity, parameter, property, term, and so forth used in the present specification and claims are to be understood as being modified in all instances by the term "about." As used herein, the term "about" means that the characteristic, item, quantity, parameter, property, or term so qualified encompasses a range of plus or minus ten percent above and below the value of the stated characteristic, item, quantity, parameter, property, or term. Accordingly, unless indicated to the contrary, the numerical parameters set forth in the specification and attached claims are approximations that may vary. At the very least, and not as an attempt to limit the application of the doctrine of equivalents to the scope of the claims, each numerical indication should at least be construed in light of the number of reported significant digits and by applying ordinary rounding techniques. Notwithstanding that the numerical ranges and values setting forth the broad scope of the invention are approximations, the numerical ranges and values set forth in the specific examples are reported as precisely as possible. Any numerical range or value, however, inherently contains certain errors necessarily resulting from the standard deviation found in their respective testing measurements. Recitation of numerical ranges of values herein is merely intended to serve as a shorthand method of referring individually to each separate numerical value falling within the range. Unless otherwise indicated herein, each individual value of a numerical range is incorporated into the present specification as if it were individually recited herein.

The terms "a," "an," "the" and similar referents used in the context of describing the present invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the present invention and does not pose a limitation on the scope of the invention otherwise claimed. No language in the present specification should be construed as indicating any non-claimed element essential to the practice of the invention.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the present invention so claimed are inherently or expressly described and enabled herein.

All patents, patent publications, and other publications referenced and identified in the present specification are individually and expressly incorporated herein by reference in their entirety for the purpose of describing and disclosing, for example, the compositions and methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A capsule dosage form comprising:
   a pharmaceutical composition comprising at least 30 mg of isotretinoin or a pharmaceutically acceptable salt or ester thereof: and
   a pharmaceutically acceptable excipient;
   wherein the size of the capsule is 1 to 4.

2. The capsule dosage form of claim 1, wherein said pharmaceutical composition comprises a liquid composition.

3. The capsule dosage form of claim 1, wherein said pharmaceutical composition comprises a semi-solid composition.

4. The capsule dosage form of claim 2, wherein said capsule is size 2 or smaller.

5. The capsule dosage form of claim 2, wherein said capsule is size 3 or smaller.

6. The capsule dosage form of claim 2, wherein said capsule is size 4.

7. The capsule dosage form of claim 5, wherein said pharmaceutical composition comprises at least 45 mg isotretinoin or a pharmaceutically acceptable salt or ester thereof.

8. The capsule dosage form of claim 4, wherein the ratio of isotretinoin or a pharmaceutically acceptable salt or ester thereof to isotretinoin or a pharmaceutically acceptable salt or ester thereof and pharmaceutically acceptable excipients is at least 0.2:1.

9. The capsule dosage form of claim 1, wherein the pharmaceutically acceptable excipient is selected from one or more oil or lipid vehicle, one or more surfactant, one or more co-surfactant and one or more antioxidant and combinations thereof.

10. The capsule dosage form of claim 1, wherein the pharmaceutically acceptable excipient is selected from one or more oil or lipid vehicle, one or more surfactant, one or more co-surfactant and one or more antioxidant and combinations thereof.

11. The capsule dosage form of claim 1, wherein the pharmaceutical composition contains about 30 to 60 mg of isotretinoin, about 5-70% by weight of an oily vehicle, 20-80% by weight of surfactant, about 1-10% by weight of co-surfactant and about 0.1-5% by weight of antioxidant.

12. The capsule dosage form of claim 1, wherein the pharmaceutical composition contains about 30 to 60 mg of isotretinoin, about 5-70% by weight peppermint oil, 20-80% by weight polyoxyl 35 castor oil, about 1-10% by weight of propylene glycol monocaprylate and about 0.1-5% by weight of butylated hydroxyl anisole and butylated hydroxyl toluene.

13. A method for the preparation of a high dose oral pharmaceutical composition comprising isotretinoin or a pharmaceutically acceptable salt or ester thereof and at least one pharmaceutical excipient, wherein the process comprises the steps of:
  (i) heating a mixture of oil, surfactant and co-surfactant at 40° C.-45° C.;
  (ii) dissolving antioxidants to the mixture of step (i) at 40° C.-45° C. and then cooling to room temperature;
  (iii) dispersing isotretinoin to step (ii) under stirring;
  (iv) optionally, the step (iii) is followed by addition of co-solvent;
  (v) optionally, the step (iii) is followed by milling;
  (vi) filling the mixture of step (iii) or step (iv) or step (v) in hard gelatin capsule;
  (vii) preparing a gelatin banding solution by soaking gelatin in water for 6 hours at room temperature, followed by addition of polysorbate 80 at temperature of 60±10° C.; and
  (viii) banding the filled capsule of step (vi) with banding solution of step (vii).

14. A method of treating a skin disorder comprising administering to a patient the capsule dosage form of claim 1.

15. The method of claim 14, wherein said skin disorder comprises one of acne, lupus, erythematous, and icthyosis.

16. The method of claim 15, wherein said skin disorder comprises acne.

17. The method of claim 16 wherein said acne comprises severe recalcitrant node acne.

18. The method of claim 17 wherein said patient is at least 12 years old.

* * * * *